US005696144A

United States Patent [19]
Royalty et al.

[11] Patent Number: 5,696,144
[45] Date of Patent: Dec. 9, 1997

[54] PROTECTION OF CORN

[75] Inventors: Reed Nathan Royalty, Raleigh; Michael Thomas Pilato; Nicholas Mark Hamon, both of Cary; Vernon L. Miles, Burlington, all of N.C.

[73] Assignee: Rhone-Poulenc Inc., Research Triangle Park, N.C.

[21] Appl. No.: 431,416

[22] Filed: May 1, 1995

[51] Int. Cl.$^6$ ........................................ A01N 43/56
[52] U.S. Cl. ............................ 514/404; 514/407
[58] Field of Search ............................ 514/404, 407

[56] References Cited

U.S. PATENT DOCUMENTS

| | | | |
|---|---|---|---|
| 5,187,185 | 2/1993 | Outcalt et al. | 514/408 |
| 5,232,940 | 8/1993 | Hatton et al. | 514/407 |

FOREIGN PATENT DOCUMENTS

| | | |
|---|---|---|
| 93/04036 | 5/1994 | Brazil. |
| 0295117 | 12/1988 | European Pat. Off. . |
| 0372982 | 6/1990 | European Pat. Off. . |
| 0460940 | 12/1991 | European Pat. Off. . |
| 87/03781 | 7/1987 | WIPO . |
| 93/06089 | 4/1993 | WIPO . |
| 94/21606 | 9/1994 | WIPO . |

OTHER PUBLICATIONS

Showers et al, *European Corn Borer–Development and Management*, North Central Regional Extension Publication No. 327, Iowa State University, Ames, IA, 1989, pp. 1–33.
Colliot et al, "FIPRONIL: A New Soil and Foliar Broad Spectrum Insecticide" in *Prot. Conf. Pest. Dis. 1992*, vol. 1, pp. 29–34 (Brighton Crop Protection Conference, Nov. 23–25, 1992).
Harrison et al, *Journal of Economic Entomology*, vol. 64, No. 6, pp. 1496–1499 (1971).
Edwards et al, *Journal of Economic Entomology*, vol. 65, No. 4, pp. 1129–1132 (1972).
Hills et al, *Journal of Economic Entomology*, vol. 65, No. 6, pp. 1697–1700 (1972).
McWhorter et al, *Journal of Economic Entomology*, vol. 69, No. 3, pp. 419–420.
Raemisch et al, *Journal of Economic Entomology*, vol. 76, No. 3, pp. 654–656 (1983).
Straub, *Journal of Economic Entomology*, vol. 76, No. 2, pp. 345–348 (1983).
"How a Corn Plant Develops", Special Report No. 48, Iowa State University of Science and Technology, Cooperative Extension Service, Ames, Iowa, ed. J. Clayton Herman (revised Feb. 1982). (pp. 1–21).

Furadan® 4F Product Label, Mar. 1994 (pp. 48–51).
*Arthropod Management Tests*, vol. 19, report No. 41F, p. 206, Entomological Society of America, Special Publication, 1994 (Rice).
*Arthropod Management Tests*, vol. 19, report No. 43F p. 207, Entomological Society of America, Special Publication, 1994 (Seymour et al.).
*Doane's Agricultural Report*, vol. 59, No. 26, p. 5 (Jun. 28, 1996).
*Arthropod Management Tests*, vol. 20, report No. 29F, pp. 168–169, Entomological Society of America, published no earlier than Jul. 10, 1995 (Fuller et al.).
*Arthropod Management Tests*, vol. 20, report No. 30F, pp. 169–170, Entomological Society of America, published no earlier than Jul. 10, 1995 (Haas et al).
*Arthropod Management Tests*, vol. 20, report No. 49F, p. 185, Entomological Society of America, published no earlier than Jul. 10, 1995 (Witkowski).
*Arthropod Management Tests*, vol. 20, report No. 50F, p. 185, Entomological Society of America, published no earlier than Jul. 10, 1995 (Witkowski).
*Arthropod Management Tests*, vol. 20, report No. 99F, p. 225, Entomological Society of America, Special Publication, published no earlier than Jul. 10, 1995 (Bernhardt).
*Arthropod Management Tests*, vol. 20, report No. 100F, pp. 225–226, Entomological Society of America, Special Publication, published no earlier than Jul. 10, 1995 (Bernhardt).
*Arthropod Management Tests*, vol. 20, report No. 101F, p. 226, Entomological Society of America, Special Publication, published no earlier than Jul. 10, 1995 (Bernhardt).
*Arthropod Management Tests*, vol. 20, report No. 103F, pp. 227–228, Entomological Society of America, Special Publication, published no earlier than Jul. 10, 1995 (Pahrang et al).
*Arthropod Management Tests*, vol. 20, report No. 104F, p. 228, Entomological Society of America, Special Publication, published no earlier than Jul. 10, 1995 (Way et al).

*Primary Examiner*—Allen J. Robinson
*Attorney, Agent, or Firm*—Burns, Doane, Swecker & Mathis, L.L.P.

[57] ABSTRACT

Method of control of corn borers attacking or susceptible or expected to attack corn plants whereby an effective amount of a 1-aryl pyrazole insecticidally active ingredient is applied near the corn sown seed.

Method of protection of corn plants against European corn borer, whereby an effective amount of a 1-aryl pyrazole insecticidally active ingredient is applied near the corn sown seed.

30 Claims, No Drawings

PROTECTION OF CORN

The present invention relates to a method of protection of corn plants against European corn borer.

There is a need for protection of corn plant against corn borers, especially those of the Pyralid moth family such as European corn borer [Latin name: Ostrinia spp. e.g. *Ostrinia nubilalis* (hereafter referred to as European corn borer)], Southwestern corn borer and Lesser cornstalk borer. These various corn borers are creating similar problems. The attack of corn plants are very dangerous because European corn borer larvae consume up to 40% of total plant leaf tissue, substantially reducing photosynthesis and subsequent yield. Consumption of ears by late-season infestations further reduces yield. European corn borer also feeds by tunneling into the stalk; tunneling causes the stalk to weaken and break under stormy or windy conditions, resulting in total loss of yield.

Furthermore, attacks are not apparent because feeding occurs unobserved in whorls and in tunnels in the stalk, therefore insecticidal treatments may be deemed unnecessary, or may be incorrectly timed so as to fail to control the larvae before they enter the whorl cluster or penetrate into the hard stalk of the plant.

The hidden effects of European corn borer and the difficulty of correctly timing foliar insecticide applications create a need to have a long and continuous protection of corn plant against European corn borer in order to avoid unpredictable introduction of said European corn borer in the whorl and stem of the plant. However, existing insecticides that must be applied to foliage for effective control let hardly an expectation of duration of protection which is longer than one or two weeks.

The difficulty in correctly timing applications could be overcome by an at-plant soil application, but this method is hardly expected to be highly effective against European corn borer with moderate amount of active ingredient, due to the interval between application of product to the soil and infestation of European corn borer (two to four months), and the distance from the soil to the foliage where the European corn borer larvae feed (0.7 m to 2.5 m).

It is known that corn plants may protected by some heterocyclic insecticides such as those described in patent applications WO 87/3781, 93/6089, 94/21606 as well as in European patent application 295117.

An object of the instant invention is to provide an effective method of treatment of corn against European corn borer despite all the existing bias against such a method. An object of the instant invention is to provide a highly effective method of treatment of corn against European corn borer.

An object of the instant invention is to provide a method of treatment of corn against European corn borer which is effective during a long period of time.

These and other objects will better appear during the description of the invention.

It has now been found that the object can be fitted and met by mean of the instant invention.

The invention is now directed to a method of control of corn borers (such as European corn borer) attacking or susceptible or expected to attack corn plants, as well as a method of protection of corn plants against corn borers (such as European corn borer), whereby an effective amount of a 1-aryl pyrazole insecticidally active ingredient is applied near the corn sown seed.

The invention is also directed to a method to reduce and/or prevent tunnels formation in corn stalks, whereby an effective amount of a 1-aryl pyrazole insecticidally active ingredient is applied near the corn sown seed.

The invention is still further directed to a method of control of corn borers (such as European corn borer) attacking or susceptible or expected to attack grown corn plants, as well as a method of protection of grown corn plants against corn borers (such as European corn borer), whereby an effective amount of a 1-aryl pyrazole insecticidally active ingredient is applied near the corn sown seed at the time of sowing.

The invention is also directed to a method to reduce and/or prevent tunnels formation in corn stalks, whereby an effective amount of a 1-aryl pyrazole insecticidally active ingredient is applied near the corn sown seed.

The 1-arylpyrazole compounds which can be used according to the instant invention are compounds of formula (I):

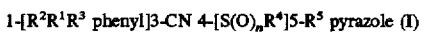

1-[$R^2R^1R^3$ phenyl]3-CN 4-[$S(O)_nR^4$]5-$R^5$ pyrazole (I)

wherein $R^1$ and $R^2$ may represent a hydrogen or halogen atom in the 2 and/or 6 position on the phenyl ring (at least one of them is preferably other than hydrogen), $R^3$ may represent a halogen atom or a haloalkyl or haloalkoxy or $SF_5$ group, in the 4 position on the phenyl ring, $R^4$ may represent an alkyl or haloalkyl group, $R^5$ may represent an amino group which may be mono- or di- substituted by an alkyl or haloalkyl radical, acyl, alkoxycarbonyl, n is 0, 1 or 2.

The alkyl, alkoxy or acyl groups of the formula (I) are preferably lower alkyl, alkoxy or acyl, that is to say radicals having one to four carbon atoms.

A preferred group of effective 1-arylpyrazoles of the present invention are those wherein:

$R^1$ and $R^2$ are a halogen atom, $R^3$ is 4-haloalkyl $R^4$ is lower haloalkyl and $R^5$ is amino.

Preferred insecticide is 1-[2,6-$Cl_2$ 4-$CF_3$ phenyl] 3-CN 4-[SO—$CF_3$]5-$NH_2$ pyrazole (compound A).

The preparation of compounds of formula (I) may be made according to any process described in patent applications WO 87/3781, 93/6089, 94/21606 as well as in European patent application 295117, or other process according to the knowledge of a man skilled in the art of chemical synthesis.

As already said, the 1-arylpyrazoles of this invention have to be applied near the sown corn seed. Practically, this means that the active ingredient should be applied either on the corn seed to be sown (application before sowing, optionally as a direct corn seed treatment), or as a soil treatment after sowing the said corn seed.

The application of active ingredient to the soil at or after corn seed sowing is advantageously done so as to provide on the soil a rate of active ingredient of from about 0.01 kg/ha to about 1 kg/ha of active ingredient, preferably between 0.02 and 0.3 kg/ha.

Advantageously, the above-said 1-arylpyrazoles may be formulated as flowable compositions, wettable powders, microemulsions and the like, all of which lend themselves to soil, water and/or foliage application and provide the requisite plant protection. Such formulations include the compounds of the invention admixed with inert, agronomically-acceptable solid or liquid diluents. The preferred formulations for soil applications are granules.

A description of possible formulations may be found in patent applications WO 87/3781, 93/6089, 94/21606 as well as in European patent application 295 117.

For example, wettable powders, dusts and dust concentrate formulations of the active ingredient of the invention can be prepared by grinding together an 1-arylpyrazole compound of formula (I), with about 1% to 20% by weight of a solid anionic surfactant. One suitable anionic surfactant is a dioctyl ester of sodium sulfosuccinic acid. About 85% to 99%, by weight, of an inert solid diluent, such as montmorillonite, attapulgite, chalk, talc, kaolin, diatomaceous earth, limestone, silicates or the like is also included in such formulations, as well as other adjuvants as previously indicated.

As already said, the 1-arylpyrazoles of this invention may also be effective for controlling European corn borer when applied to the corn before sowing. The corn may be treated, especially by coating or embedding or impregnation or soaking or dipping in liquid or paste formulations which are known per se and are subsequently dried. Corn comprising 2 to 1000 gram per quintal, preferably 5 to 800 g/q are particularly appropriate.

The invention is especially advantageous be cause of the long treatment it provides. Protection for a duration corresponding to a growth of about 40 to 50 cm of the stem of the corn plant may be obtained according to the invention.

The following examples are presented as illustrations of the present invention.

EXAMPLE 1

Corn was sown in 3.5 l. pots, and grown in a greenhouse. Compounds A granules (1.5 % w/w) were applied on the soil surface at sowing time at a rate equivalent to 120 g/ha of active ingredient. European corn borer egg masses were pinned to the foliage 3 to 4 weeks after plant emergence. Numbers of tunnels in stalks caused by European corn borer larvae were counted 4 to 5 weeks after infestation (plants were then higher than 2 m.). Untreated controls, and plants treated with Terbufos (1120 g/ha) and Imidacloprid (500 g/ha) granules averaged 5.3, 5.5, and 5.6 tunnels/stalk, respectively. Plants treated with compound A averaged 0.4 tunnel/stalk.

EXAMPLE 2

Corn seeds were treated with compound A at a rate of 500 g. of compound A per quintal of seed. The experiment was then done as described in Example 1. Plants had at the end an average of 1.3 tunnel/stalk. Untreated plants had an average of 4.1 tunnel/stalk.

What is claimed is:

1. A method for protecting corn plants in need of protection against corn borer, said method comprising applying, on or near the sown corn seed from which said plants grow, an amount effective to protect corn plants against corn borer of a compound of the formula:

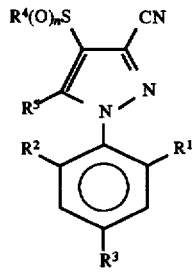

wherein:

each of $R^1$ and $R^2$ is hydrogen or halogen;

$R^3$ is halogen, $C_1-C_4$ haloalkyl, $C_1-C_4$ haloalkoxy or $SF_5$;

$R^4$ is $C_1-C_4$ alkyl or $C_1-C_4$ haloalkyl;

$R^5$ is amino which is monosubstituted or disubstituted by $C_1-C_4$ alkyl, $C_1-C_4$ haloalkyl, $C_1-C_4$ acyl or ($C_1-C_4$ alkoxy)carbonyl; and n is 0, 1 or 2.

2. A method according to claim 1, wherein the corn borer is European corn borer.

3. A method according to claim 1, wherein, in the compound of formula (I), $R^1$ is halogen, $R^2$ is halogen, $R^3$ is $C_1-C_4$ haloalkyl, $R^4$ is $C_1-C_4$ haloalkyl and $R^5$ is amino.

4. A method according to claim 3, wherein the compound of formula (I) is 5-amino-3-cyano-1-(2,6-dichloro-4-trifluoromethylphenyl)-4-trifluoromethylsulfinylpyrazole.

5. A method according to claim 1, wherein the compound of formula (I) is applied as a soil treatment after sowing the corn seed.

6. A method according to claim 1, wherein the compound of formula (I) is applied so as to provide a rate of active ingredient of from about 0.01 kg/ha to about 1 kg/ha.

7. A method according to claim 5, wherein the compound of formula (I) is applied so as to provide a rate of active ingredient of from about 0.01 kg/ha to about 1 kg/ha.

8. A method according to claim 6, wherein the rate of active ingredient is between 0.02 and 0.3 kg/ha.

9. A method according to claim 7, wherein the rate of the active ingredient is between 0.02 and 0.3 kg/ha.

10. A method according to claim 1, wherein the corn plants are protected up to a height of 2 meters or more.

11. A method according to claim 1, wherein the corn plants are protected for a period of time exceeding two months.

12. A method for protecting corn plants in need of protection against corn borer, said method comprising applying to the corn seed from which said plants grow an amount effective to protect corn plants against corn borer of a compound of the formula:

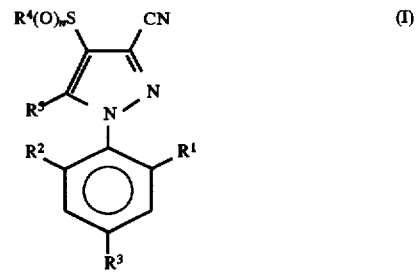

wherein:

each of $R^1$ and $R^2$ is hydrogen or halogen;

$R^3$ is halogen, $C_1-C_4$ haloalkyl, $C_1-C_4$ haloalkoxy or $SF_5$;

$R^4$ is $C_1-C_4$ alkyl or $C_1-C_4$ haloalkyl;

$R^5$ is amino which is monosubstituted or disubstituted by $C_1-C_4$ alkyl, $C_1-C_4$ haloalkyl, $C_1-C_4$ acyl or ($C_1-C_4$ alkoxy)carbonyl; and n is 0, 1 or 2.

13. A method according to claim 12, wherein the corn borer is European corn borer.

14. A method according to claim 12, wherein, in the compound of formula (I), $R^1$ is halogen, $R^2$ is halogen, $R^3$ is $C_1-C_4$ haloalkyl, $R^4$ is $C_1-C_4$ haloalkyl and $R^5$ is amino.

15. A method according to claim 14, wherein the compound of formula (I) is 5-amino-3-cyano-1-(2,6-dichloro-4-trifluoromethylphenyl)-4-trifluoromethylsulfinylpyrazole.

16. A method according to claim 12, wherein the compound of formula (I) is applied so as to provide corn seed comprising from 2 to 1000 grams of active ingredient per quintal.

17. A method according to claim 16, wherein the compound of formula (I) is applied so as to provide corn seed comprising from 5 to 800 grams of active ingredient per quintal.

18. A method for protecting corn plants in need of protection against corn borer, said method comprising applying to the corn seed from which said plants grow, at the time of sowing, an amount effective to protect corn plants against corn borer of a compound of the formula:

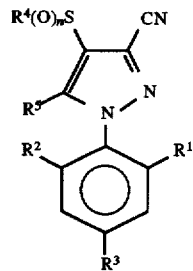

wherein:

each of $R^1$ and $R^2$ is hydrogen or halogen;
$R^3$ is halogen, $C_1$–$C_4$ haloalkyl, $C_1$–$C_4$ haloalkoxy or $SF_5$;
$R^4$ is $C_1$–$C_4$ alkyl or $C_1$–$C_4$ haloalkyl;
$R^5$ is amino which is monosubstituted or disubstituted by $C_1$–$C_4$ alkyl, $C_1$–$C_4$ haloalkyl, $C_1$–$C_4$ acyl or ($C_1$–$C_4$ alkoxy)carbonyl; and
n is 0, 1 or 2.

19. A method according to claim 18, wherein the corn borer is European corn borer.

20. A method according to claim 18, wherein, in the compound of formula (I), $R^1$ is halogen, $R^2$ is halogen, $R^3$ is $C_1$–$C_4$ haloalkyl, $R^4$ is $C_1$–$C_4$ haloalkyl and $R^5$ is amino.

21. A method according to claim 20, wherein the compound of formula (I) is 5-amino-3-cyano-1-(2,6-dichloro-4-trifluoromethylphenyl)-4-trifluoromethylsulfinylpyrazole.

22. A method for reducing or preventing tunnel formation caused by corn borer in the stalks of corn plants, said method comprising applying, on or near the sown corn seed from which said plants grow, an amount effective to reduce or prevent tunnel formation in the stalks of corn plants of a compound of the formula:

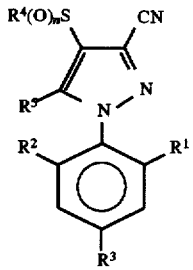

wherein:

each of $R^1$ and $R^2$ is hydrogen or halogen;
$R^3$ is halogen, $C_1$–$C_4$ haloalkyl, $C_1$–$C_4$ haloalkoxy or $SF_5$;
$R^4$ is $C_1$–$C_4$ alkyl or $C_1$–$C_4$ haloalkyl;
$R^5$ is amino which is monosubstituted or disubstituted by $C_1$–$C_4$ alkyl, $C_1$–$C_4$ haloalkyl, $C_1$–$C_4$ acyl or ($C_1$–$C_4$ alkoxy)carbonyl; and
n is 0, 1 or 2.

23. A method according to claim 22, wherein, in the compound of formula (I), $R^1$ is halogen, $R^2$ is halogen, $R^3$ is $C_1$–$C_4$ haloalkyl, $R^4$ is $C_1$–$C_4$ haloalkyl and $R^5$ is amino.

24. A method according to claim 23, wherein the compound of formula (I) is 5-amino-3-cyano-1-(2,6-dichloro-4-trifluoromethylphenyl)-4-trifluoromethylsulfinylpyrazole.

25. A method for reducing or preventing tunnel formation caused by corn borer in the stalks of corn plants, said method comprising applying to the corn seed from which said plants grow an amount effective to reduce or prevent tunnel formation in the stalks of corn plants of a compound of the formula:

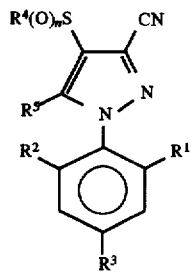

wherein:

each of $R^1$ and $R^2$ is hydrogen or halogen;
$R^3$ is halogen, $C_1$–$C_4$ haloalkyl, $C_1$–$C_4$ haloalkoxy or $SF_5$;
$R^4$ is $C_1$–$C_4$ alkyl or $C_1$–$C_4$ haloalkyl;
$R^5$ is amino which is monosubstituted or disubstituted by $C_1$–$C_4$ alkyl, $C_1$–$C_4$ haloalkyl, $C_1$–$C_4$ acyl or ($C_1$–$C_4$ alkoxy)carbonyl; and
n is 0, 1 or 2.

26. A method according to claim 25, wherein, in the compound of formula (I), $R^1$ is halogen, $R^2$ is halogen, $R^3$ is $C_1$–$C_4$ haloalkyl, $R^4$ is $C_1$–$C_4$ haloalkyl and $R^5$ is amino.

27. A method according to claim 26, wherein the compound of formula (I) is 5-amino-3-cyano-1-(2,6-dichloro-4-trifluoromethylphenyl)-4-trifluoromethylsulfinylpyrazole.

28. A method for reducing or preventing tunnel formation caused by corn borer in the stalks of corn plants, said method comprising applying to the corn seed from which said plants grow, at the time of sowing, an amount effective to reduce or prevent tunnel formation in the stalks of corn plants of a compound of the formula:

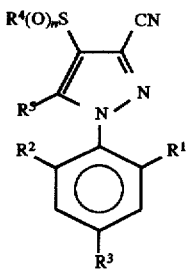

wherein:

each of $R^1$ and $R^2$ is hydrogen or halogen;
$R^3$ is halogen, $C_1$–$C_4$ haloalkyl, $C_1$–$C_4$ haloalkoxy or $SF_5$;
$R^4$ is $C_1$–$C_4$ alkyl or $C_1$–$C_4$ haloalkyl;
$R^5$ is amino which is monosubstituted or disubstituted by $C_1$–$C_4$ alkyl, $C_1$–$C_4$ haloalkyl, $C_1$–$C_4$ acyl or ($C_1$–$C_4$ alkoxy)carbonyl; and
n is 0, 1 or 2.

29. A method according to claim 28, wherein, in the compound of formula (I), $R^1$ is halogen, $R^2$ is halogen, $R^3$ is $C_1$–$C_4$ haloalkyl, $R^4$ is $C_1$–$C_4$ haloalkyl and $R^5$ is amino.

30. A method according to claim 29, wherein the compound of formula (I) is 5-amino-3-cyano-1-(2,6-dichloro-4-trifluoromethylphenyl)-4-trifluoromethylsulfinylpyrazole.

\* \* \* \* \*